US010675030B2

(12) United States Patent
Ziniti et al.

(10) Patent No.: US 10,675,030 B2
(45) Date of Patent: Jun. 9, 2020

(54) ABSORBABLE SURGICAL COIL FASTENER

(71) Applicant: C.R. Bard, Inc., Murray Hill, NJ (US)

(72) Inventors: Donald E. Ziniti, Cumberland, RI (US); John Conidi, Plainville, MA (US); Matthew Rothberg, Hopkinton, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 149 days.

(21) Appl. No.: 15/669,852

(22) Filed: Aug. 4, 2017

(65) Prior Publication Data

US 2019/0038286 A1  Feb. 7, 2019

(51) Int. Cl.
| | |
|---|---|
| *A61B 17/08* | (2006.01) |
| *A61B 17/064* | (2006.01) |
| *A61B 17/10* | (2006.01) |
| *A61B 17/00* | (2006.01) |
| *A61B 17/068* | (2006.01) |

(52) U.S. Cl.
CPC ............ *A61B 17/08* (2013.01); *A61B 17/064* (2013.01); *A61B 17/10* (2013.01); *A61B 17/068* (2013.01); *A61B 2017/00004* (2013.01); *A61B 2017/00831* (2013.01); *A61B 2017/0649* (2013.01)

(58) Field of Classification Search
CPC ..... A61B 17/064; A61B 17/068; A61B 17/08; A61B 2017/00831; A61B 2017/0649; A61B 17/1214; A61B 17/1215; A61B 17/12145; A61B 17/58; A61B 17/68; A61B 2/88; A61F 2/88
See application file for complete search history.

(56) References Cited

U.S. PATENT DOCUMENTS

| | | | | | |
|---|---|---|---|---|---|
| 5,810,851 | A | * | 9/1998 | Yoon | ............ A61B 17/06 606/139 |
| 6,544,265 | B2 | * | 4/2003 | Lieberman | ............ A61F 2/446 606/247 |
| 2011/0245861 | A1 | * | 10/2011 | Chen | ............ A61B 17/12022 606/200 |

(Continued)

FOREIGN PATENT DOCUMENTS

| | | |
|---|---|---|
| EP | 2 497 426 A1 | 9/2012 |
| WO | WO 2015/171268 A2 | 11/2015 |
| WO | WO 2016/174972 A1 | 11/2016 |

OTHER PUBLICATIONS

International Search Report and Written Opinion for International Application No. PCT/US2018/044744, dated Jan. 8, 2019.

*Primary Examiner* — Diane D Yabut
*Assistant Examiner* — Majid Jamialahmadi
(74) *Attorney, Agent, or Firm* — Wolf, Greenfield & Sacks, P.C.

(57) ABSTRACT

A surgical fastener deployment system may include a plurality of coil fasteners having a head and coil body. In some embodiments, the head is comprised of a bioabsorbable polymer. In one embodiment, the coil body may be comprised of a shell and a core and one of the shell and the core may be comprised of one of a magnesium alloy or a bioabsorbable polymer, and the other of the shell and core is formed of the other of the magnesium alloy and the bioabsorbable polymer. The coil body may also include an internal channel which may have a support coil disposed within.

6 Claims, 8 Drawing Sheets

(56) References Cited

U.S. PATENT DOCUMENTS

| | | | |
|---|---|---|---|
| 2013/0338706 A1* | 12/2013 | Jimenez | A61B 17/0057 606/213 |
| 2015/0133964 A1 | 5/2015 | Ranucci et al. | |
| 2015/0133970 A1 | 5/2015 | Ranucci et al. | |
| 2015/0133971 A1* | 5/2015 | Ranucci | A61B 17/064 606/151 |
| 2015/0133972 A1 | 5/2015 | Ranucci et al. | |
| 2015/0157767 A1* | 6/2015 | Edick | C22C 23/04 623/1.15 |
| 2017/0056007 A1* | 3/2017 | Eckert | A61B 17/068 |
| 2017/0143340 A1 | 5/2017 | Ranucci et al. | |
| 2017/0311937 A1* | 11/2017 | Bambury | A61B 17/0057 |

\* cited by examiner

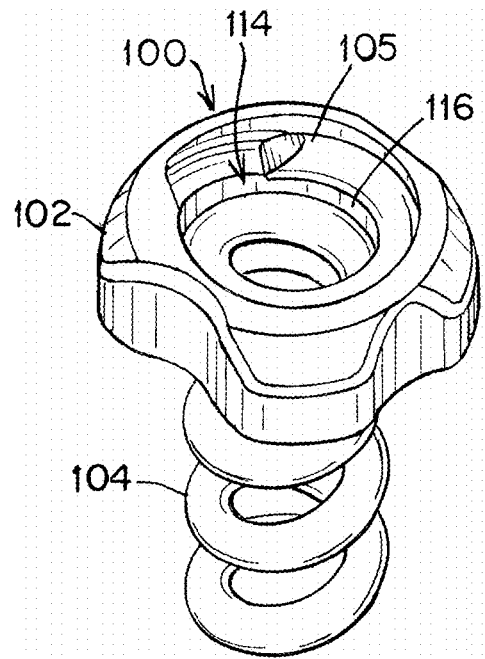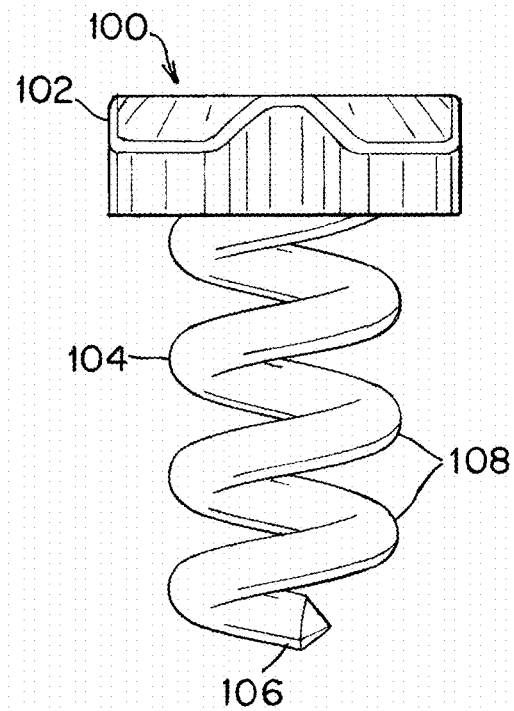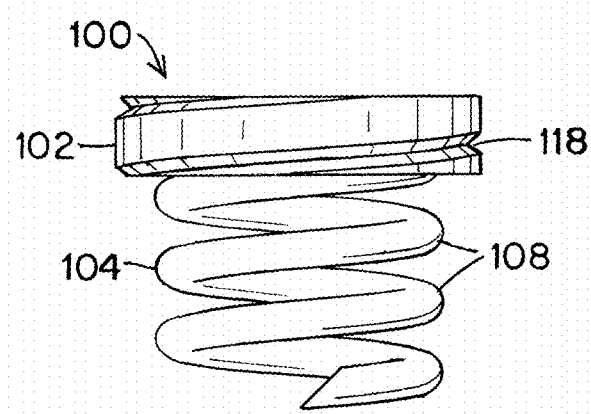

ABSORBABLE SURGICAL COIL FASTENER

FIELD

Embodiments disclosed herein are related to surgical fasteners, and more particularly, to absorbable surgical coil fasteners.

BACKGROUND

Surgical fasteners are widely used in many different medical procedures. For example, staples, sutures, clips, tacks, coil fasteners and other fastener types are commonly used in laparoscopic and open surgical procedures.

SUMMARY

The embodiments disclosed herein describe a surgical fastener. In some embodiments, the surgical fastener is composed of a head, and a coil body that extends distally from the head. The coil body could include a shell that at least partially surrounds a core, and the shell is made of a magnesium alloy or a bioabsorbable polymer, while the core could be made of whichever of the magnesium alloy or the bioabsorbable polymer that the shell is not made of. The surgical fastener could have a transverse dimension of between or equal to 0.018 to 0.035 inches. The magnesium alloy could have a yield strength of between 314 MPa to 506 MPa, and the shell could have a thickness between 0.010 to 0.20 inches.

In other embodiments, the surgical fastener is composed of a head, and a coil body extending from the head, and the coil body includes a channel that extends along at least a portion of the length of the coil body. The surgical fastener could have an opening on the proximal surface of its head, wherein the channel of the coil body may be accessible through the opening. Some embodiments have the channel extending along the interior of the coil body, while others have it external to the coil body. The channel could be constructed and arranged to receive a support such that the support is partially disposed within the channel as the surgical fastener is deployed from a deployment device.

Also disclosed is a method of applying a surgical fastener involving inserting a support into a channel formed in and extending along at least a portion of a length of a coil body of a fastener, and deploying the surgical fastener while the support is at least partially located in the channel. In some embodiments of the method, the supported is inserted into the channel through a hole formed in a head of the coil fastener, and the fastener may be rotated as it is deployed. In channel may extend along the entire length of the coil body, and the support could be removed from the channel when the surgical fastener is deployed or after the surgical fastener is deployed.

In other embodiments, the surgical fastener is composed of a head and a coil body extending distally from the head, where the coil body is composed of a magnesium alloy with a yield strength of between or equal to 314 MPa and 506 MPa, and has a transverse dimension of between or equal to 0.018-0.035 inches. The magnesium alloy could be comprised of at least magnesium, dysprosium, neodymium and/ or europium, and zinc and/or zirconium. The head of the surgical fastener could be bioabsorbable. The surgical fastener could be used in conjunction with a surgical fastener deployment system for deployment.

In other embodiments of a surgical fastener, the surgical fastener is made of a head and a coil body which extends distally from the head. The coil body in these embodiments is composed of a magnesium alloy that is 5.0%-25.5% by weight dysprosium, 0.01%-5% by weight neodymium and/ or europium, 0.1%-3.0% by weight zinc, and 0.1%-2.0% by weight zirconium. The head may be made of a bioabsorbable material. And the coil body may have windings with transverse dimensions between 0.018 inches and 0.035 inches. The surgical fastener could also be used in conjunction with a surgical fastener deployment device for deployment.

It should be understood that the foregoing concepts, and additional concepts discussed below, are described herein with reference to certain illustrative embodiments and the figures. The illustrative embodiments described herein are not necessarily intended to show all aspects, but rather are used to describe a few illustrative embodiments. Thus, aspects are not intended to be construed narrowly in view of the illustrative embodiments. In addition, it should be understood that certain features disclosed herein might be used alone or in any suitable combination with other features.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 1 is a schematic perspective view of an embodiment of a surgical fastener including threading on a through hole formed in a head of the fastener;

FIG. 2 is a schematic side view of the surgical fastener of FIG. 1;

FIG. 3 is a schematic side view of an embodiment of a surgical fastener including a thread on an external surface of a head of the fastener;

DETAILED DESCRIPTION

Figure 4:
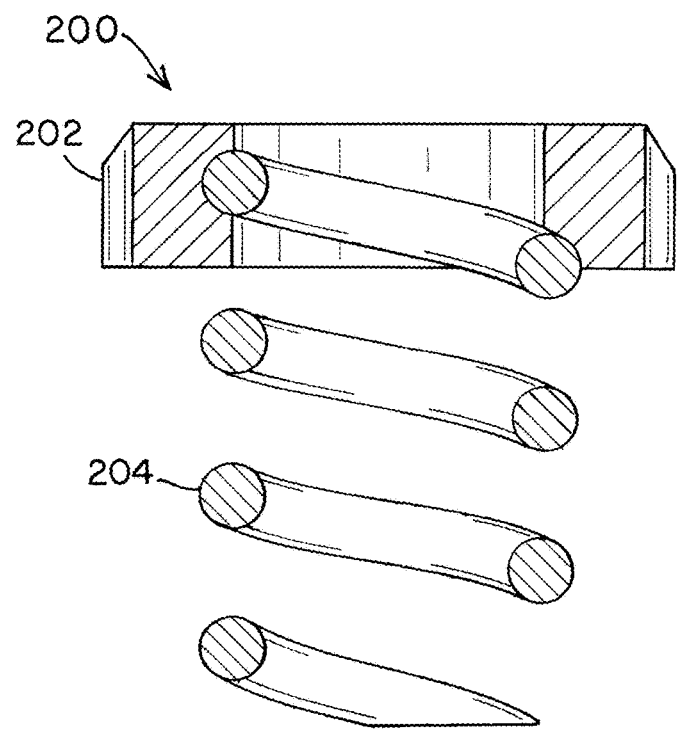
FIG. 4 is a cross-sectional view of one embodiment of a surgical fastener including a solid coil body.

The Inventors have recognized that magnesium alloys offer desirable characteristics for inclusion in a surgical fastener such as, for example, the ability to be sharpened and maintain a point as well as the biocompatibility and bioabsorption characteristics of magnesium alloys. However, prior magnesium alloys exhibited relatively low yield and tensile strengths which limited their use in surgical fasteners.

In view of the above, the Inventors have recognized the benefits associated with forming surgical fasteners with recently developed higher strength magnesium alloys and/or with composite structures to enable the formation and use of various types of coil fasteners.

In one embodiment, a surgical fastener includes a coil body composed of a magnesium alloy. In some applications, a yield strength of the magnesium alloy and a maximum transverse dimension, e.g. diameter, of a cross section of a coil winding of the coil body may be selected such that the coil body does not exhibit significant amounts of plastic (i.e. irreversible) deformation when deployed. Appropriate dimensions and materials properties of the coil body are described in further detail below.

In embodiments where a solid coil body is used in a surgical fastener, the coil winding of a coil body may have a cross section with an outer transverse dimension, e.g. diameter, that is between or equal to 0.46 mm to 0.89 mm (0.018-0.035 inches), 0.5 mm to 0.79 mm (0.020-0.031 inches), or 0.56 mm to 0.69 mm (0.022-0.027 inches). Additionally, the coil body may be made from a biocompatible and/or bioabsorbable magnesium alloy with a yield strength between or equal to 69 MPa to 506 MPa (10-73 ksi) or 206 MPa to 506 MPa (30-73 ksi) or 314 MPa to 506 MPa (45.5-73 ksi). In some embodiments, the magnesium alloy may also have a composition that is 5.0%-25.5% by weight dysprosium, 0.01%-5% by weight neodymium and/or europium, 0.1%-3.0% by weight zinc, 0.1%-2.0% by weight zirconium, 1 ppm-0.4% by weight impurities, and a balance to 100.0% by weight magnesium. However, other biocompatible and/or bioabsorbable magnesium alloys exhibiting sufficient yield strengths may also be used as well.

In another embodiment, a surgical fastener includes a composite coil body. Specifically, the composite coil body may include a coil winding that comprises a core made from a first material and a shell at least partially surrounding, and in some instances completely surrounding, an exterior perimeter of a cross section of the core made from a second different material. The shell may be disposed on the core either along an entire length of the coil body or only along a portion of the length of the coil body.

In instances where a shell of a coil winding does not completely cover the perimeter of a corresponding cross section of a core of the coil body, the shell may be positioned on any appropriate face of the coil body. For example, in one embodiment, a shell may be located on an interior side of the coil body that faces an interior of the coil body (i.e. directed toward an interior of the surgical fastener) or on an exterior side of the coil body directed outward from the surgical fastener. Thus, it should be understood that the particular orientation and arrangement of a shell on a core is not limited to only those specific embodiments described herein.

As noted above, the shell and core of a coil body may be comprised of different materials. For example, in one embodiment, the shell is either a magnesium alloy or bioabsorbable polymer and the core is the other of the magnesium alloy and bioabsorbable polymer. Therefore, in one specific embodiment, the shell is comprised of a magnesium alloy, while the core is comprised of a bioabsorbable polymer. In another specific embodiment, the shell is comprised of a bioabsorbable polymer, while the core is comprised of a magnesium alloy. However, while a magnesium alloy is specifically mentioned above, it should be understood that other types of materials including different polymers, different metallic materials, and/or any other appropriate materials may be used to form the disclosed composite coil bodies as the disclosure is not so limited.

In embodiments where a coil body of a surgical fastener comprises a core and shell, an outer transverse dimension, e.g. a thickness or a diameter, of a cross section of a coil winding of the coil body, which may be viewed as a transverse dimension of the combination of the core and shell, may be between or equal to 0.46 mm to 0.89 mm (0.018-0.035 inches), 0.5 mm to 0.79 mm (0.020-0.031 inches), or 0.56 mm to 0.69 mm (0.022-0.027 inches), though thicker and thinner coil bodies are also contemplated. The shell may have a thickness between or equal to 0.127 mm to 0.3 mm (0.005 and 0.012 inches), 0.15 mm to 0.20 mm (0.006 and 0.008 inches), or any other appropriate thickness. Correspondingly, the core may have a transverse dimension, such as a thickness or diameter, of a cross section of the core that is between or equal to 0.25 mm to 0.51 mm (0.01 inches and 0.02 inches), 0.25 mm to 0.64 mm (0.01 inches and 0.025 inches), or any other appropriate dimension including dimensions both greater and less than those noted above.

Composite coil bodies comprising a core and a shell may be manufactured in any suitable way. For example, in some embodiments, a coil body core is dipped into a liquid or molten material that may either solidify, harden, or cure to form a shell on the core. The shell material may also be overmolded onto a core of a coil body. In another embodiment, a shell is wrapped, or otherwise deformed, partially or fully around a pre-formed core to produce a final composite coil body. In such an embodiment, the composite may then be deformed into the desired shape of the coil body. In yet another embodiment where the outer shell is a magnesium alloy, or other metallic or hard material, a molten or uncured core material may be injected into an internal channel formed within a shell. The core material may then harden or cure within the channel to form the core of a composite coil body. Several of these methods are elaborated on in further detail below in regards to the figures. Of course, while specific methods and constructions have been discussed, other suitable methods of manufacturing the core and shell are also contemplated as the current disclosure is not so limited.

In some applications it may be desirable to provide a surgical fastener with a hollow coil body with a channel that extends along at least a portion of a length of the coil body. However, such a structure may not exhibit sufficient strength to be deployed without buckling or otherwise deforming. Accordingly, in some embodiments, it may be desirable to support at least a portion of the surgical coil fastener as it is being deployed. In one such embodiment, a surgical fastener includes a coil body with a shell or outer tube that forms a channel extending along at least a portion of a length of the coil body. In such an embodiment, at least a portion of the coil body's length may be supported by a support, such as a supporting coil or core during deployment of the surgical fastener. The support may be sized and shaped to selectively fit within the channel of the coil body to support, i.e. resist deformation of, the coil body during at least a portion of a deployment phase of the associated surgical fastener. The supporting coil and channel may extend through either the entire length of the coil body (i.e. form a proximal end of the coil body to a distal tip), or only through a portion of the coil body as the disclosure is not so limited. The supporting structure may be inserted into the channel when supplied to a user, during, or prior to deployment of the fastener, or in any other appropriate manner. The supporting coil may then be retained within the channel of the coil body during at least a portion of deployment of the fastener to provide the desired support to the coil body of the fastener as it is deployed into tissue, bone, and/or prosthetic devices.

In some embodiments where a support is used with a coil body, the coil body may be comprised of a magnesium alloy, but other biocompatible materials sufficiently stiff for use in surgical fastening applications are also contemplated. Further, a support, such as a supporting coil, may be made from 316 LVM stainless steel which has an ultimate tensile strength of 1503 MPa to 1641 MPa (218-238 ksi) and a yield strength of 1317 MPa to 1641 MPa (191-238 ksi) at 2.6% elongation. Other possible materials include other stainless steels, nitinol, and titanium alloys, though the current disclosure is not limited to just these materials. Further, it is contemplated that a support may be made of any other suitably stiff material capable of sufficiently supporting the coil body through a combination of a larger elastic modulus and/or thickness. Thus, through the use of these design parameters, the support may be stiffer than the coil body.

In embodiments where a support is used, a transverse dimension, such as a thickness or diameter, of a cross section of a coil winding of a coil body may be between or equal to 0.46 mm to 0.89 mm (0.018-0.035 inches), 0.5 mm to 0.79 mm (0.020-0.031 inches), or 0.56 mm to 0.69 mm (0.022-0.027 inches). Correspondingly, a channel formed in the coil windings may have a transverse dimension, such as a width or diameter of the channel, that is between or equal to 0.13 mm to 0.64 mm (0.005 to 0.025 inches), 0.25 mm to 0.51 mm (0.010 to 0.020 inches), or any other appropriate dimension. The support may be correspondingly sized and shaped to be insertable and removeable from the channel within the coil body. However, while specific dimensions for the coil windings, support and channels are described above, different dimensions both larger and less than those noted above are contemplated as well.

In some embodiments, the above noted surgical fasteners including coil bodies may be attached to a corresponding head. In such a configuration, the coil bodies may be attached to and extend distally from the heads. The head may also be configured to have a transverse dimension that is larger (wider and/or greater in diameter), than an outer transverse dimension of the coil body to engage and secure underlying material and/or tissue. In addition to helping with fixation of tissue and prosthetics, the head of a surgical fastener may include one or more features that cooperate with corresponding features of a delivery device for driving the fastener from the device and into an implantable prosthesis and/or tissue, bone, or muscle. For example, a head may have a through hole including one or more threads formed within the through hole that interact with a threaded mandrel to deploy the fastener. Alternatively, in another embodiment one or more threads may be formed on an exterior perimeter of the head to interact with a threaded tube that the surgical fastener is positioned in to deploy the fastener.

A head may be attached to a surgical fastener in any number of ways. For example, depending on the embodiment, the head may include an internal thread that is threaded to the coil body and attaches the head to a proximal end of the coil body. In another embodiment, the head may be secured to the coil body with a compression or press fit between the head and a proximal portion of the coil body. The head may include a cavity, such as a counterbore or a through hole, that receives the portion of the coil body therein to provide the compression or press fit. More specifically, the portion of the coil body received in the cavity may have an outer transverse dimension in a relaxed state that is larger than, or equal to, a transverse dimension of the cavity to create the compression or press fit as the coil body is threaded to the head. The portion of the coil body received in the cavity may include approximately a half turn or more of at least one coil, or other feature associated with the coil body. In yet another embodiment, a coil body may be attached to a head by overmolding the head onto a proximal portion of the coil body. While certain constructions are noted above, it should be understood that the various attachment methods may be combined with one another and other types of attachment methods may be used as the disclosure is not so limited.

Depending on the embodiment, a distal end of a coil body may be configured to penetrate an implantable prosthesis, bone, muscle and/or tissue. In such an embodiment, the distal tip of the coil body could be sharpened or blunt depending on the characteristics of the target tissue. The distal end of the coil body could also be comprised of a different material than the rest of the coil body. The distal end may be comprised of a biocompatible material such as stainless steel, nitinol, titanium or any other sufficiently stiff to penetrate tissue, but also malleable enough to be easy to blunt or sharpen when compared to the rest of the coil body.

Appropriate bioabsorbable polymers that may be used with the above noted embodiments, include, but are not limited to, a poly(lactic-co-glycolic acid) (PLGA), a poly (lactide-co-glycolide)s (PLG, such as Purasorb PLG 8218), a poly(lactic acid) (PLLA), or any other suitable biocompatible and/or bioabsorbable polymer.

Again, it should be understood that any appropriate magnesium alloy, or other appropriate biocompatible and/or bioabsorbable metal or metal alloy, may be used with the above embodiments. However, in one embodiment, a shell, core, or other component of a coil body may be made from a biocompatible and/or bioabsorbable magnesium alloy with a yield strength between or equal to 69 MPa to 506 MPa (10-73 ksi), 206 MPa to 506 MPa (30-73 ksi) or 314 MPa to 506 MPa (45.5-73 ksi). One such exemplary magnesium alloy includes Resoloy manufactured by MeKo which may have a composition that is 5.0%-25.5% by weight dysprosium, 0.01%-5% by weight neodymium and/or europium, 0.1%-3.0% by weight zinc, 0.1%-2.0% by weight zirconium, 1 ppm-0.4% by weight impurities, and a balance to 100.0% by weight magnesium. This particular alloy may have an ultimate tensile strength of 461 MPa (66.8 ksi), and a yield strength of 403 MPa (58.5 ksi) at 2.6% elongation. However, other biocompatible magnesium alloys of sufficient strength for surgical applications are contemplated as well.

In addition to the above, in some embodiments, the materials used to form a head and coil body of a surgical fastener are capable of either being sterilized before, during, or after assembly and packaging to maintain sterility, and/or is sterilizable for use.

In the above noted embodiments, a length of a coil body extending distally from a distal face of an associated head may be between or equal to approximately 3 mm to 6.5 mm, 4 mm to 5.5 mm, or 4.5 mm to 5 mm. The coil body may also include approximately 2.5 turns to approximately 6 turns of coil windings. An outer transverse dimension of the coil body may be between or equal to approximately 2.5 mm to approximately 4.9 mm (0.098 inches to 0.193 inches). Thus, the coil body may be sized and shaped to facilitate deployment of the surgical fasteners through a 5 mm cannula. A pitch of the coil windings of the coil body may also be between or equal to approximately 0.7 mm to approximately 1.1 mm (0.03 to 0.045 inches). However, other coil body lengths, head lengths, outer transverse dimensions and pitches greater than or less than the previously stated values are also contemplated as the current disclosure is not limited to the above values.

In some embodiments, a head attached to a coil body has an outer transverse dimension that is between or equal to approximately 2.7 mm to approximately 4.98 mm (0.106 inches to 0.196 inches) or 3.0 mm to 4.6 mm (0.12 inches to 0.18 inches) or 3.5 mm to 4.1 mm (0.14 inches to 0.16 inches). A thickness of the head, corresponding to a thickest portion of the head in a direction orthogonal to the outer transverse dimension, may also be between or equal to approximately 0.97 mm (0.030 inches) to approximately 1.02 mm (0.04 inches). Of course, while particular dimensions are given above for a coil body and head, it should be understood that a surgical fastener may employ a coil body and head having any suitable sizes and configurations for a desired application as the disclosure is not so limited.

The above described embodiments of a surgical fastener may be used for various surgical fastening applications. For example, the surgical fastener may be used to attach an implantable prosthesis, such as a soft tissue repair fabric, to tissue and/or muscle. Other non-limiting applications for the fastener may involve joining portions of tissue and/or muscle together, joining portions of tissue and/or muscle to bone, and/or joining an implantable prosthesis to bone and/or tissue. Of course, the currently disclosed surgical fasteners may be employed for other applications as well as the disclosure is not so limited.

Turning now to the figures, several non-limiting embodiments are described in further detail. However, it should be understood that the various features and components described in relation to the figures may be used either individually and/or in any appropriate combination as the disclosure is not so limited.

In one illustrative embodiment, as shown in FIGS. 1 and 2, a surgical fastener 100 may include a coil body 104 and a separate head 102 that is attached to a proximal end of the coil body 105. Depending on the embodiment, the distal end of the coil body 106 may be configured for penetrating an implantable prosthesis, tissue, muscle, and/or bone. In one embodiment, the distal end 106 may include a sharp distal tip, although the distal end may employ any suitable configuration, including a blunt distal tip, as the disclosure is not limited in this fashion.

As also depicted in the figures, a coil body 104 may include one or more coil windings 108 corresponding to one or more full turns of the coil body extending distally from the head. For example, the depicted coil body includes coil windings that form approximately four full turns extending distally form the head. A transverse dimension of a cross section of a coil winding of the coil body may correspond to a diameter or thickness of the material used to form the coil windings of the coil body.

As illustrated in the figures, the coil windings 108 may be arranged in a helical or spiral configuration suitable for driving the fastener into and through prosthetic material, tissue, muscle and/or bone. Thus, in some embodiments a coil body may be cylindrical in shape with a circular cross-section, though non-circular cross-sectional shapes of both the coil body and/or coil winding such as triangular, square, pentagonal, rectangular, or any other appropriate shape also are contemplated. The coil body 104 may include any number of coil windings 108 with any desired spacing or pitch between the coil windings and any transverse dimension, including outer and inner transverse dimensions, suitable for a particular application. In some embodiments an outer transverse dimension of the coil body is constant along a length of the coil body. However, if desired, one or more of the coil windings of the coil body may have different transverse dimensions relative to each other. For example, the coil body may include coil windings that have an outer transverse dimension that decreases in a distal direction to form a coil body with a conical or tapered shape.

As shown in FIGS. 1-2, to facilitate deployment of the surgical fastener, in some embodiments, a head 102 of a surgical fastener may include a through hole 114 that passes from a proximal face of the head to an opposing distal face of the head. Additionally, an internal thread 116 is formed on an inner surface of the through hole. As described further below, the threaded through hole may be used in conjunction with a threaded mandrel of a deployment device that is received in the through hole to deploy the surgical fastener. Alternatively, in another embodiment, as depicted in FIG. 3, threads 118 formed on an external surface of the head interact with threading on a corresponding deployment device to deploy the surgical fastener. Of course, while threaded fasteners have been depicted above, embodiments, in which fasteners are deployed using features other than threading are also contemplated. For example, a head of the surgical fastener may include one or more features that mechanically interlock with a deployment device to permit it to be rotated and distally displaced during deployment as the disclosure is not limited to any particular deployment method.

FIG. 4 shows a cross-sectional view of one embodiment of a surgical fastener 200. The surgical fastener includes a head 202 and a solid magnesium alloy coil body 204. The head is located at a proximal end of the fastener and the coil body extends distally from the head. In some embodiments, once deployed into tissue, the head and coil body may be absorbed by the body.

Figure 5:
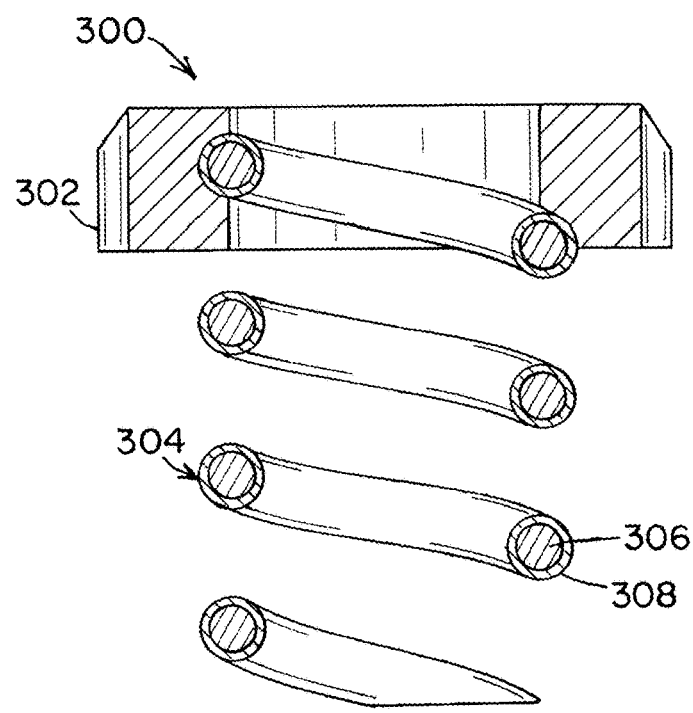
FIG. 5 is a cross-sectional view of one embodiment of a surgical fastener including a composite coil body including a core and shell comprised of different materials.

FIG. 5 shows a cross-sectional view of another embodiment of a surgical fastener 300. In the depicted embodiment, the surgical fastener includes a head 302 and coil body 304. In this embodiment, the coil body 304 is made from a composite coil winding including a core 306 and shell 308. The shell at least partially, and in the depicted embodiment completely, encapsulates or surrounds an outer perimeter of the core. The core and shell may be made from different materials as previously discussed. In one specific embodiment, the core and shell are made from a biocompatible magnesium alloy and a biocompatible polymer, and the head is made from a biocompatible polymer as described above. Additionally, in some embodiments, the shell, the core, and/or head are made from bioabsorbable materials so that they may be absorbed by the body. Of course, other materials for the core, shell, and/or head are also contemplated as the current disclosure is not limited to only the aforementioned materials.

Figure 6:
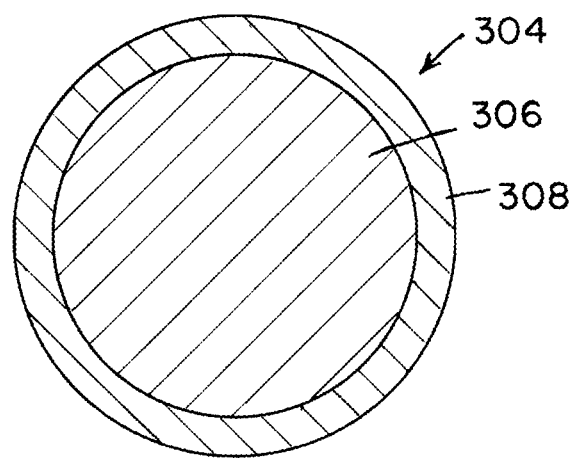
FIG. 6 is a cross-sectional view of one embodiment of a coil body with a shell overmolded around a core of the coil body.
Figure 7:
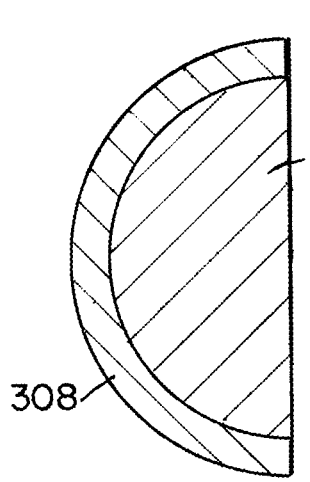
FIG. 7 is a cross-sectional view of one embodiment of a coil body with a shell that partially encompasses a core of the coil body.
Figure 8:
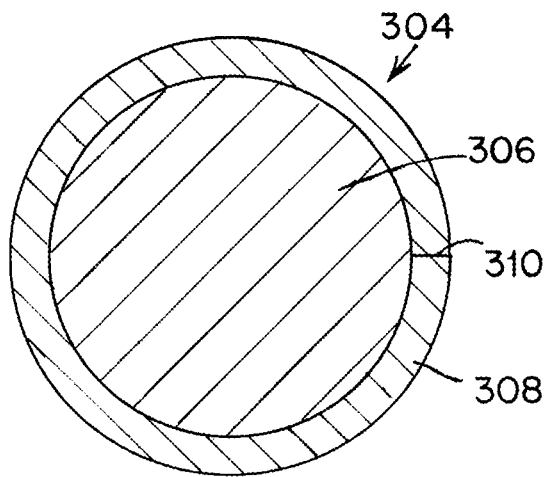
FIG. 8 is a cross-sectional view of one embodiment of a coil body with a shell deformed around a core of the coil body.

FIGS. 6, 7, and 8 show cross-sectional views of different embodiments of composite coil windings 304 including cores 306 and shells 308. The depicted composite coil windings include different shapes and may be manufactured in different ways.

FIG. 6 shows a cross-section of a coil winding 304 of a coil body where the shell 308 has been overmolded onto the core 306 to fully encapsulate the core. Other embodiments of the coil may be formed from spin-coating, or dip-coating, or the shell material being sprayed onto the core. Of course, other suitable methods of producing a shell may also be employed.

FIG. 7 shows an embodiment of a coil winding 304 of a coil body where the core 306 is partially encapsulated by the shell 308. In such an embodiment, the core of the coil body is at least partially exposed to a surrounding environment. In the depicted embodiment, the shell covers the rounded portion of a semi-circular core. However, other shapes of the core such as circular, square, triangular, and rectangular may be used. Additionally, the shell may cover any desired portion of the core's outer surface as the disclosure is not so limited. Further, despite the non-circular cross-section, the coil body still winds around and forms a helical shape with the core partially exposed to the environment for at least part of the coil. Additionally, the coil body may be arranged such that any portion of the cross section of the depicted coil winding may be oriented either inwards or outwards relative to the coil body as the disclosure is not so limited. For example, in one embodiment, the exposed surface of the core may be oriented such that it faces inwards relative to the coil body. However, in another embodiment, the exposed surface of the core may be oriented such that it faces outwards relative to the coil body. In the above embodiments, the shell may be formed on the core in a number of ways including, but not limited to overmolding, lamination, deformation of the shell onto the core, or any other appropriate method of attaching the core to the coil body.

FIG. 8 shows an embodiment of a coil body where a shell 308 has been applied by wrapping, rolling, or otherwise deforming a preformed sheet onto a preformed core 306. A seam 310 may be present along a length of the coil body in instances where the shell fully surrounds the core. Once the core and shell are assembled the composite structure may be wound into a helical structure to form a coil body.

Figure 9A:
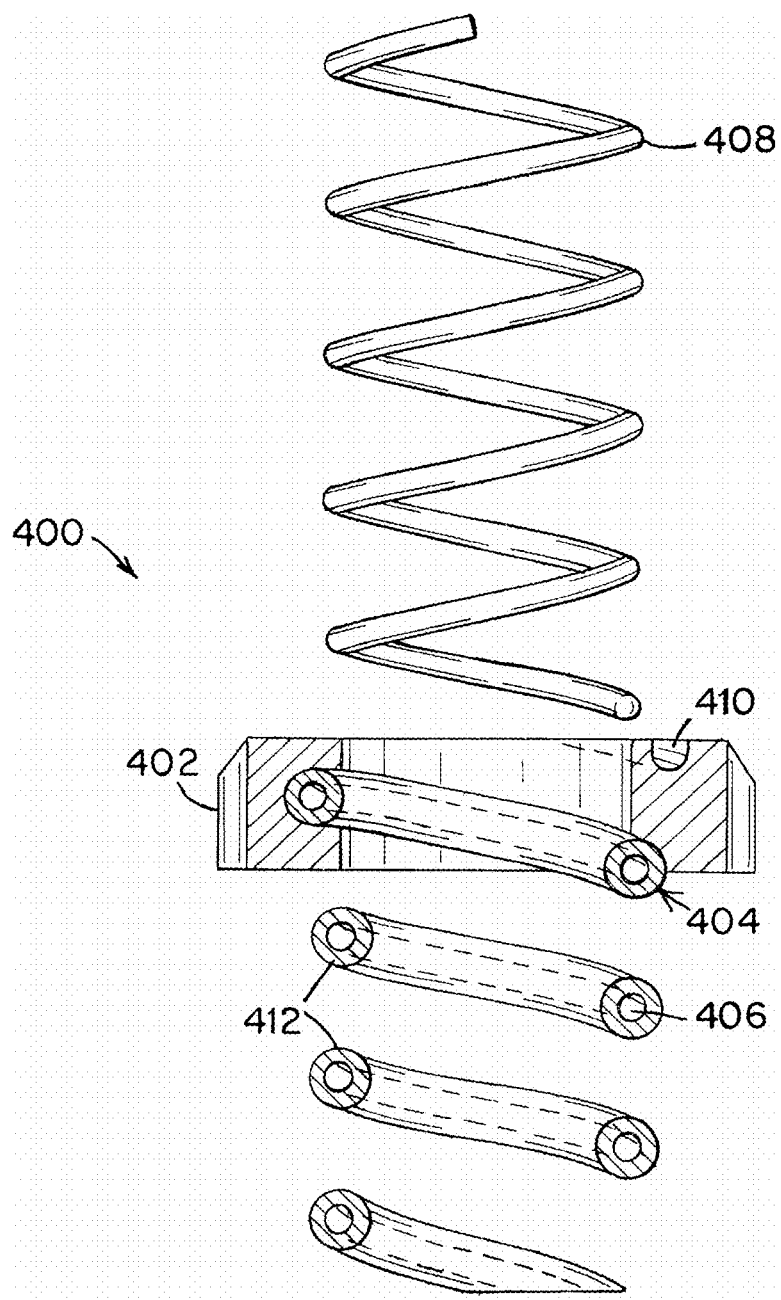
FIG. 9a is a cross-sectional view of one embodiment of a surgical fastener where a coil body is internally supported by a selectively insertable support core, prior to the insertion of the support core.
Figure 9B:
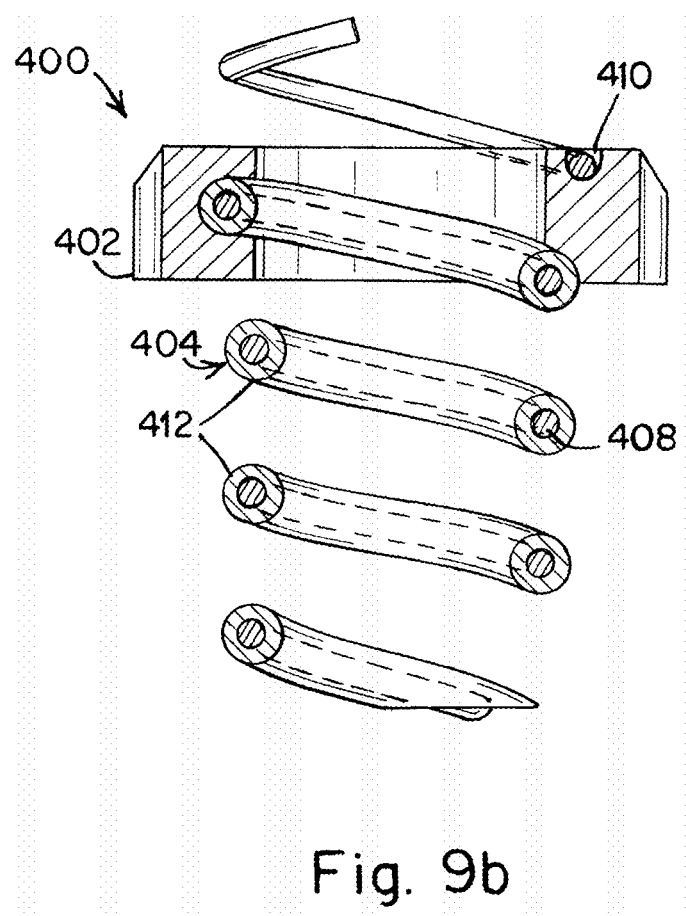
FIG. 9b is a cross-sectional view of the surgical fastener of FIG. 7a after insertion of the support core into the coil body.

FIGS. 9a and 9b show a cross-sectional view of one embodiment of a surgical fastener 400 that is supported by a stiffer support, such as a support coil 408, during deployment. In the depicted embodiment, the surgical fastener includes a hollow channel 406 that is formed within the coil windings 412 and extends along at least a portion of a length of the coil body 404. In some embodiments, the channel of the coil body extends up to and is accessible through an opening 410 formed in the head 402. The opening may either be located on a proximal face of the head and/or a surface of a through hole formed in the head. In either case, the channel and opening are shaped and sized such that the support coil 408 may be inserted into the opening and channel.

FIG. 9a shows the support coil 408 as it is being inserted into the opening 410 in the head and channel 406 of the coil body. As the support coil is rotated relative to the fastener, the support coil is threaded into the channel of the coil body. FIG. 9b shows the support coil fully threaded into the channel and coil body. In this embodiment, the support, corresponding to the support coil, extends out from a distal end of the coil body. However, embodiments, in which a support and channel do not extend out from a distal end of a coil body are also contemplated.

In reference to the above embodiment, during deployment of a surgical fastener the support coil 408, or other support, may be disposed in the channel 406. The surgical fastener, and in some embodiments the support coil, are then rotated and advanced distally to deploy the surgical fastener. Either during, or after the surgical fastener, is deployed, the support coil may be rotated relative to the surgical fastener to remove the support coil from the corresponding channel of the surgical fastener. For example, the support may extend to a distal tip of an associated deployment device and held stationary relative to the deployment device and surgical fastener. Therefore, as the surgical fastener is rotated relative to the support coil, it is advanced distally with the support coil located within a portion of the channel still within the deployment device. Accordingly, the support coil will support a portion of the surgical fastener exiting the distal tip of the device as it enters into the corresponding tissue, bone, and/or prosthetic. Alternatively, the surgical fastener and support coil may be rotated and advanced distally together to support an entire length of the coil body as it is deployed into the corresponding tissue, bone, and/or prosthetic. The support coil may then be rotated relative to the surgical fastener to remove it from the corresponding channel after deployment. Of course, it should be understood that other methods and arrangements for deploying a surgical fastener with a support are also contemplated as the disclosure is not limited to any particular system or arrangement.

Figure 10A:
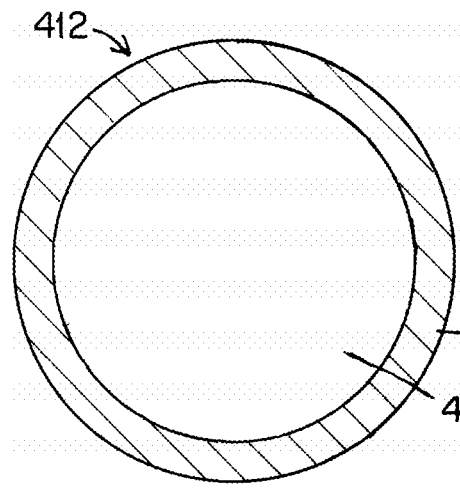
FIG. 10a is a cross-sectional view of one embodiment of a coil body winding including a hollow internal channel.
Figure 10B:
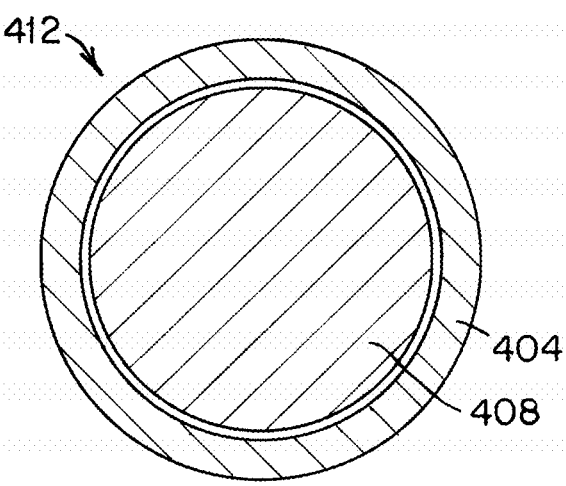
FIG. 10b is a cross-sectional view of the coil body winding of FIG. 10a with a support core inserted into the channel.

FIGS. 10a and 10b show a cross-sectional view of a coil winding of a coil body constructed to accommodate a support. FIG. 10a shows the coil body with a coil winding 404 including an empty inner channel 406. FIG. 10b shows the support coil 408 inserted into the channel.

Figure 11A:
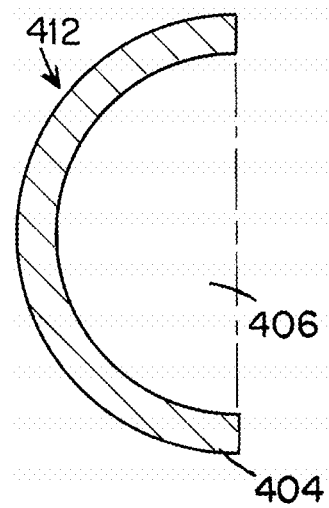
FIG. 11a is a cross-sectional view of one embodiment of a coil body winding including an open channel extending along a length of the coil body.
Figure 11B:
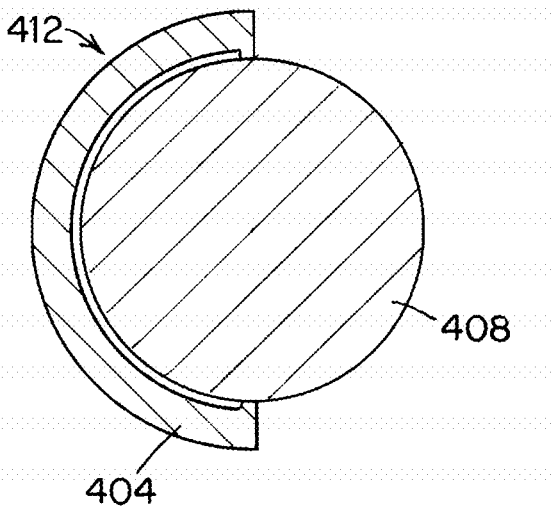
FIG. 11b is a cross-sectional view of the coil body winding of FIG. 11a with a support core inserted into the open channel.

FIGS. 11a and 11b show an embodiment of a coil body including an externally located channel. In the depicted embodiment a semi-circular coil winding 412 includes a semi-circular channel 406 formed on an exterior surface of the coil winding. FIG. 11b depicts a support, such as the support coil 408, inserted into the exterior channel which may still support the coil body during deployment even though the channel does not fully surround the support coil. Of course, differently shaped coil windings and channels including square, rectangular, pentagonal, and triangular to name a few may also be used. The resulting coil winding may still be shaped into a helix to form a coil body. Additionally, the channel may be located on an inward facing surface of the coil winding directed towards an interior of the coil body or an exterior surface of the coil winding directed outwards from the coil body interior as the disclosure is not so limited.

Figure 12:
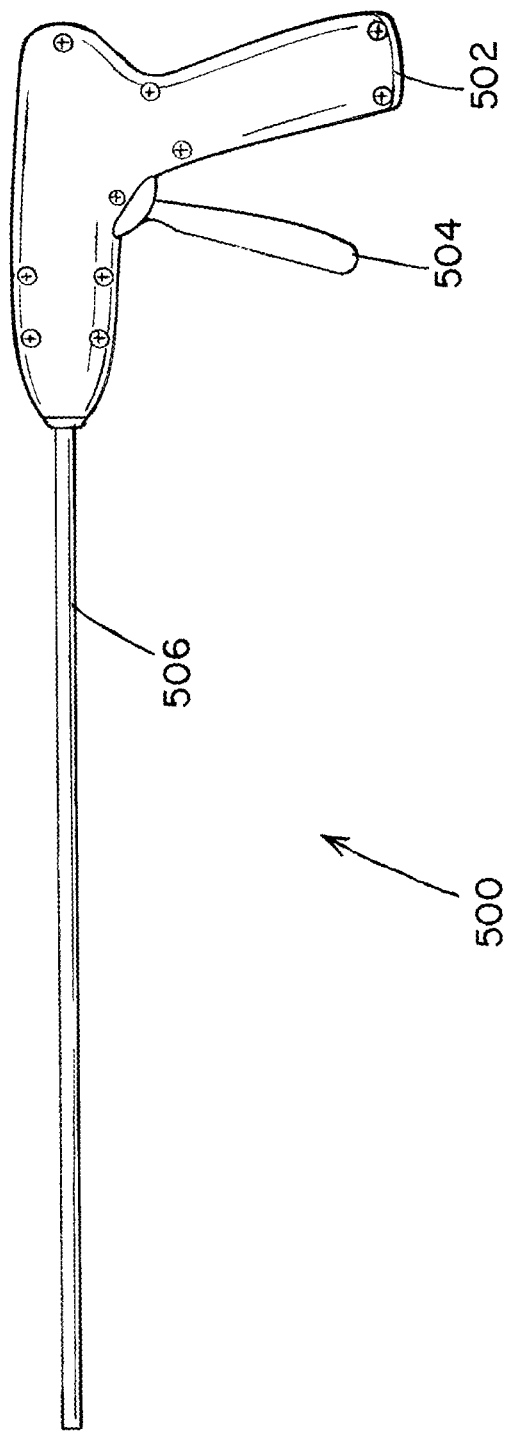
FIG. 12 is a schematic side view of an exemplary deployment device that could be used to deploy the disclosed surgical fasteners.
Figure 13A:
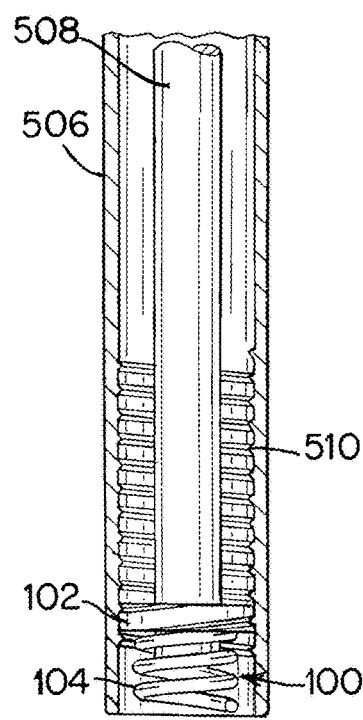
FIGS. 13a-13c are cross-sectional views of a deployment device loaded with a surgical fastener during deployment.
Figure 13B:
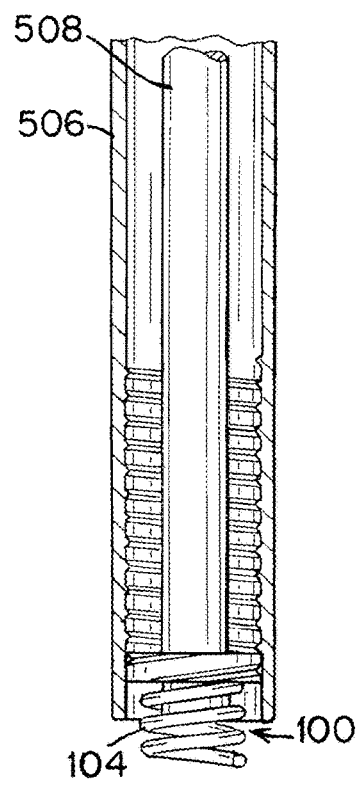
Figure 13C:
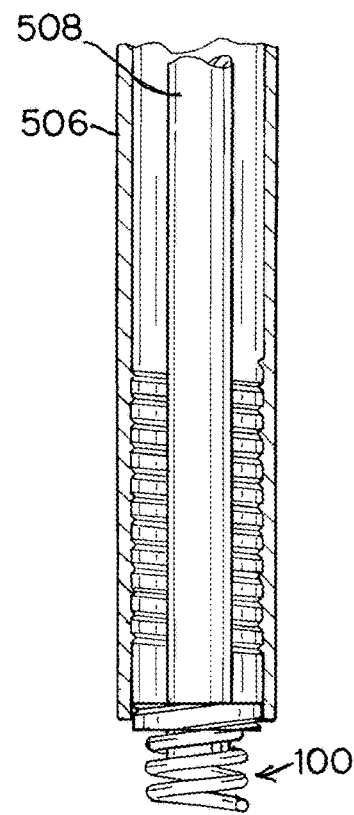

The various embodiments of a surgical fastener described herein may be delivered to a surgical site using a delivery device that imparts rotation to the fastener and drives the fastener into prosthetic material, tissue, muscle and/or bone. As shown in FIG. 12, one embodiment of a delivery device 500 may include a handle 502 including a trigger 504 at a proximal end of the device. The delivery device 500 may also include an outer tube or cannula 506 extending in a distal direction from the handle 502. As shown in FIGS. 13a-13c, in some embodiments, the delivery device may include a mandrel 508 that extends along a length of the outer tube or cannula 506 for supporting and/or guiding one or more fasteners 100 within the cannula. The mandrel is configured to rotate one or more surgical fasteners 100 positioned on the mandrel when the mandrel is rotated relative to the outer tube when the trigger is actuated. Threaded heads 102 of the fasteners are then rotated relative to threading 510 formed on an internal surface of the outer tube. Rotation of the fasteners 100 relative to the threaded outer tube in turn provides a reactive thrust to the fasteners causing the fasteners to be driven in a distal direction along the length of the mandrel 508, out of a distal end of the outer tube 506, and into the prosthetic material and/or tissue.

In embodiments of the surgical fastener that include a channel within the coil body and a delivery device including a support, the fasteners may be pre-loaded into the delivery device with the support already disposed within the channel. In some embodiments, the delivery device is additionally designed to insert the support into at least a distal most fastener as it is deployed. The support may then be removed from the coil body either during or after deployment of the surgical fastener as described previously above.

While a laparoscopic delivery device has been depicted in the above figures, the current disclosure is not so limited. Instead, the currently disclosed surgical fasteners may be used with any appropriate device capable of deploying the disclosed surgical fasteners. For example, while a threaded tubular member has been depicted in the figures, embodiments in which a stationary threaded mandrel and rotatable outer tube are used are also contemplated. Additionally, the surgical fasteners could also be used in other delivery devices such as an endoscopic device, a borescopic device, a catheter, a surgical instrument for use in "open" procedures, or any other appropriate surgical instrument.

It should be understood that the foregoing description of various aspects of at least one embodiment of the current disclosure are intended merely to be illustrative thereof and that other embodiments, modifications, and equivalents of the invention are within the scope of the invention recited in the claims appended hereto. Accordingly, the foregoing description and drawings are by way of example only.

What is claimed is:

1. A surgical fastener comprising:
    a head including an opening formed in the head, wherein the opening is formed on a proximal face of the head; and
    a coil body separately formed from the head, wherein the coil body is attached to and extends distally from the head, wherein the coil body includes a channel extending along at least a portion of a length of the coil body, wherein the channel of the coil body is accessible through the opening, and wherein the opening is radially offset from a central portion of the head.

2. The surgical fastener of claim 1, wherein the channel of the coil body is an internal channel of the coil body.

3. The surgical fastener of claim 1, wherein the channel of the coil body is an external channel.

4. The surgical fastener of claim 1, wherein the channel extends along an entire length of the coil body.

5. The surgical fastener of claim 1, wherein the channel is constructed and arranged to receive a support at least partially disposed within the channel when the surgical fastener is deployed from a fastener deployment device.

6. A surgical fastener deployment system in combination with the surgical fastener of claim 5, wherein the surgical fastener deployment system is configured to deploy the surgical fastener and the surgical fastener deployment system includes the support, wherein the support is constructed and arranged to be positioned within the channel and support the surgical fastener during at least a portion of a deployment of the surgical fastener.

* * * * *